United States Patent
Hintz (10) Patent No.: US 9,636,509 B2
(45) Date of Patent: May 2, 2017

(54) RETRIEVAL OF INFORMATION FROM AN IMPLANTABLE MEDICAL DEVICE

(75) Inventor: William J. Hintz, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1076 days.

(21) Appl. No.: 13/359,557

(22) Filed: Jan. 27, 2012

(65) Prior Publication Data
US 2013/0198463 A1 Aug. 1, 2013

(51) Int. Cl.
- *H04Q 5/22* (2006.01)
- *A61N 1/378* (2006.01)
- *A61N 1/08* (2006.01)
- *A61N 1/37* (2006.01)

(52) U.S. Cl.
CPC ............. *A61N 1/3787* (2013.01); *A61N 1/08* (2013.01); *A61N 1/3708* (2013.01)

(58) Field of Classification Search
None
See application file for complete search history.

(56) References Cited

U.S. PATENT DOCUMENTS

| | | | | |
|---|---|---|---|---|
| 4,481,950 A * | 11/1984 | Duggan | ............... | A61N 1/3708 607/29 |
| 4,952,864 A * | 8/1990 | Pless | ......................... | A61N 1/08 323/299 |
| 6,016,448 A * | 1/2000 | Busacker | ............. | A61N 1/3708 607/29 |
| 6,127,799 A | 10/2000 | Krishnan | | |
| 6,282,407 B1 | 8/2001 | Vega et al. | | |
| 7,240,833 B2 | 7/2007 | Zarembo | | |
| 7,787,958 B2 | 8/2010 | Stevenson | | |
| 7,812,731 B2 | 10/2010 | Bunza et al. | | |
| 7,876,228 B2 | 1/2011 | Kroll et al. | | |
| 7,883,019 B2 | 2/2011 | Kang et al. | | |
| 7,916,013 B2 | 3/2011 | Stevenson | | |
| 2002/0099895 A1* | 7/2002 | Landron | ............... | G06F 1/1632 710/303 |
| 2003/0114899 A1* | 6/2003 | Woods | ............... | A61N 1/36071 607/60 |

(Continued)

FOREIGN PATENT DOCUMENTS

| EP | 1704893 A1 | 9/2006 |
|---|---|---|
| GB | 2428802 A | 2/2007 |

(Continued)

OTHER PUBLICATIONS

(PCT/US2013/023089) PCT Notification of Transmittal of the International Search Report and the Written Opinion of the International Searching Authority, Mailed Apr. 10, 2013, 10 pages.

*Primary Examiner* — Curtis King (57) ABSTRACT

Techniques for retrieving information from an implantable medical device (IMD) having a depleted internal energy source such as a non-rechargeable battery are disclosed. The IMD is powered by and communicates with an external interrogation device to access a memory location of the IMD and for transfer of the information in the memory location to the external interrogation device subsequent to depletion of the internal energy source. In an embodiment, the memory location is included in a non-volatile memory component of the IMD to maintain the information stored in the memory component.

26 Claims, 5 Drawing Sheets

(56) References Cited

U.S. PATENT DOCUMENTS

| | | |
|---|---|---|
| 2003/0183226 A1 | 10/2003 | Brand et al. |
| 2004/0113790 A1 | 6/2004 | Hamel et al. |
| 2004/0185913 A1* | 9/2004 | Aoshima ............ G01R 31/3651 |
| | | 455/566 |
| 2005/0206555 A1* | 9/2005 | Bridgelall ................. G01S 5/14 |
| | | 342/127 |
| 2005/0258242 A1 | 11/2005 | Zarembo |
| 2008/0048855 A1 | 2/2008 | Berger |
| 2008/0065181 A1 | 3/2008 | Stevenson |
| 2008/0183247 A1 | 7/2008 | Harding |
| 2009/0015413 A1* | 1/2009 | Gelabert et al. ........... 340/572.1 |
| 2009/0043203 A1* | 2/2009 | Pelissier .................. A61B 8/00 |
| | | 600/446 |
| 2009/0157145 A1 | 6/2009 | Cauller |
| 2009/0209849 A1 | 8/2009 | Rowe et al. |
| 2009/0234200 A1 | 9/2009 | Husheer |
| 2010/0085160 A1* | 4/2010 | Fu ............................... 340/10.1 |
| 2010/0161003 A1* | 6/2010 | Malmberg ............. A61N 1/025 |
| | | 607/60 |
| 2011/0057037 A1 | 3/2011 | Frysz et al. |
| 2011/0270025 A1* | 11/2011 | Fridez .................. A61F 5/0059 |
| | | 600/37 |
| 2012/0053657 A1* | 3/2012 | Parker .................... H02J 7/025 |
| | | 607/61 |
| 2013/0060103 A1* | 3/2013 | Bergida et al. ............... 600/302 |

FOREIGN PATENT DOCUMENTS

| | | |
|---|---|---|
| WO | 2006/116489 A2 | 11/2006 |
| WO | 2010/042020 A1 | 4/2010 |
| WO | 2010/059376 A1 | 5/2010 |

* cited by examiner

RETRIEVAL OF INFORMATION FROM AN IMPLANTABLE MEDICAL DEVICE

FIELD

This disclosure relates generally to the field of implantable medical systems and more particularly to retrieval of information from an implantable medical device having a depleted internal energy source.

BACKGROUND

Implantable devices exist that electrically stimulate body tissue to treat or relieve the symptoms of a wide variety of physiological or psychological maladies. Such devices are typically part of systems that are entirely implantable within the patient or are partially implantable and partially external to the patient. Systems that are entirely implantable in the patient typically include an implantable medical device and an extension and lead or leads. In such a system, the implantable medical device, extension and lead are entirely implanted in the bodies of the patients.

A programmer is used outside the patient's body and communicates with the implantable medical device by both sending and receiving information to and from the implantable medical device. The programmer is used to interrogate the implantable medical device and set and adjust the device operation, including the parameters of the therapy, to be most effective. Some examples of the programmer may include a computer having a programming head and a printer. The programming head may be placed over the implantable medical device to interrogate and program desired device settings using telemetry. Alternatively, the communication may be through RF communication. The programming head also receives information from the implantable medical device such as the current electrical parameters or status information.

Such implantable devices are often powered by an internal battery which permits the device to function continuously over a long period of time. Often for implantable medical devices, the internal battery used to power the device's circuitry is non-rechargeable. The battery is included in the implantable device, which in turn is surgically implanted and is typically intended to be physically inaccessible. The batteries used in conjunction with the implantable medical device are not intended to and is typically not replaceable or rechargeable. As such, the operational lifetime of the device is limited to the duration of battery life which may range from approximately three (3) years to approximately eight (8) years.

It may be desirable to obtain information from the implantable medical device when it ceases to operate such as due to the power source being completely drained. Current processes rely on returned implantable medical devices to understand failure modes and causes, and also to verify non-failure. However, due to the power source of the implantable medical device being depleted, the device cannot be interrogated via telemetry. In the case of devices that have already been implanted, the current processes are limited to implantable medical devices that can be explanted. However, future devices cannot or are not intended to be explanted and as such it is impossible to retrieve any desired information. An ability to monitor the performance of implantable medical devices is required and critical to identifying any issues that require corrective action.

What is needed are methods, devices and systems to facilitate transfer of data from the powerless IMD to an external device.

SUMMARY

In conventional devices, it is generally common to explant implantable devices that have a depleted power source for access of information stored in the device. Such information may be useful for studying the device operation over the device's lifetime, gleaning the therapy efficacy of the device through retrieval of physiological information of the patient, and retrieval of any information that may not have been transmitted by the device prior to depletion of the power source. In general, the disclosure is directed towards methods, devices, and systems for retrieving information from the implantable medical devices that have a depleted power source.

In an embodiment, a passively energized circuit is provided for retrieval of information from an implantable medical device to a remotely located interrogating device, independent of a power source that is physically coupled to the device. An energy harvesting circuit is provided for sourcing energy from an external device to power the passively energized circuit. In an example, the external device may be the interrogating device. The energy harvesting circuit may be coupled to a telemetry module of the implantable medical device to obtain energy for powering one or more components of the implantable device.

In another embodiment, the energy harvested by the passively energized circuit enables memory-to-memory transfer of information from a memory location of the implantable medical device to a non-volatile memory. The memory to memory transfer of information to the non-volatile memory may be performed in response to an interrogation operation by the interrogation device.

In an embodiment, the information retrieved by the interrogating device reflects a device status or failure mode of the implantable medical device prior to battery depletion. Prior to battery depletion, the information is continually updated as appropriate by the implantable device during normal operation, so that the latest status at device expiration is stored and retrievable indefinitely. The information is retrievable by the interrogation device, even after the device is no longer active and the energy in the battery has been depleted.

DETAILED DESCRIPTION OF THE DRAWINGS

Illustrative embodiments of the disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Some patient disorders may be treated via delivery of stimulation to a target tissue site within the patient. For example, an implantable medical device ("IMD") may be implanted within the patient and positioned to deliver electrical stimulation to the target tissue site via a plurality of electrodes. For IMDs that are not planned to be explanted, or that cannot be explanted, the final operating status and/or information stored within the device may not be known when the energy source of the IMD is depleted. As such, the disclosure is directed towards methods, devices, and systems for retrieving information from the implantable medical devices that have a depleted power source.

Figure 1:
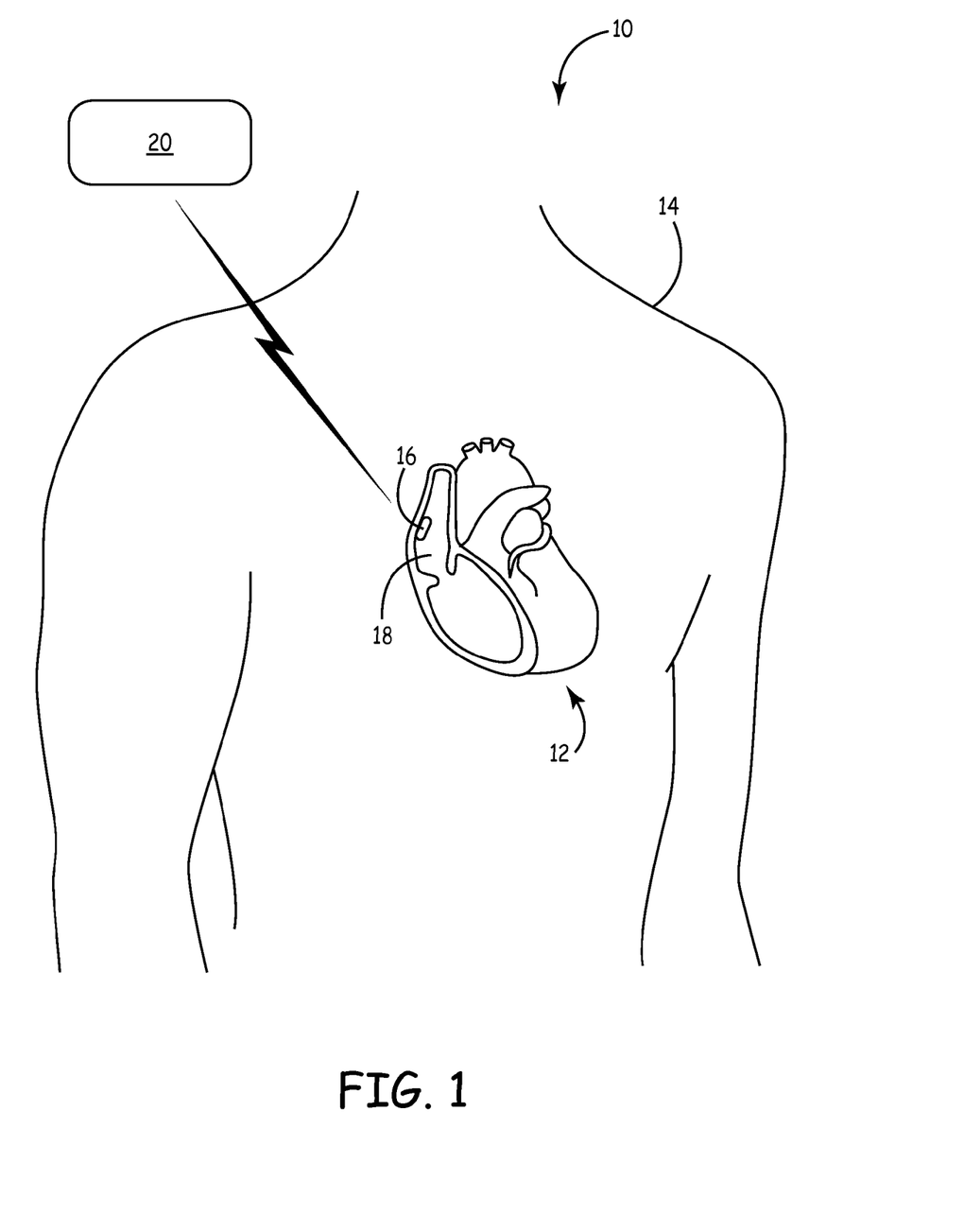
FIG. 1 is a conceptual diagram illustrating an example therapy system for treating a cardiac disorder of patient.

FIG. 1 is a conceptual diagram illustrating an example therapy system 10 for treating a cardiac disorder of patient 14. System 10 includes leadless IMD 16 and external interrogation device 20, which may communicate with one another, e.g., via wireless telemetry. In the example illustrated in FIG. 1, external interrogation device 20 may be an external programmer and leadless IMD 16 is implanted within right atrium 18 of heart 12 of patient 14, proximate to the sinoatrial (SA) node of patient 14. In other examples, leadless IMD 16 may be implanted proximate to another portion of heart 12 of patient 14.

Leadless IMD 16 may provide one or more advantages. For example, a leadless IMD may eliminate the need for an implantable lead, and may also require a smaller power source such that a stimulator of the IMD may be positioned directly at the target tissue site. Example leadless pacemakers and neurological stimulators are described in, for example, U.S. Pat. No. 3,943,936 which issued to Rasor et al. on Mar. 16, 1976, entitled "Self Powered Pacers and Stimulators," and which is incorporated herein by reference in its entirety.

Although the example systems and techniques are primarily described herein with respect to delivering electrical stimulation to the target tissue site via a plurality of housing electrodes, in other examples, the systems and techniques may be applicable to other types of stimulation of the target tissue site. In addition, although the example systems and techniques are primarily described herein with respect to delivering electrical stimulation to a target tissue site within or on heart 12 of patient 14 to treat a cardiac disorder, in other examples, the systems and techniques may be applicable to stimulation of other types of target tissue sites. For example, the systems and techniques may be utilized to excite cells that are found in skeletal, smooth muscle, pancreatic, and neural tissue. In some examples, the systems and techniques described herein are applicable to deep brain stimulation for the treatment of Parkinson's disease or stimulation of the spinal cord or peripheral nerves for the treatment of pain. In some examples, the systems and techniques described herein may be used to deliver stimulation to target tissue sites within the brain or spinal cord of patient 14, gastrointestinal tissue to support gastrointestinal therapy such as therapy to address obesity, motility disorders (e.g., gastroparesis), dyspepsia, or other therapies, pelvic floor tissue (e.g., sacral or pudendal nerve tissue) to support pelvic floor therapy such as pain therapy, urinary or fecal incontinence therapy, sexual dysfunction, or other therapies, or cranial tissue to support cranial nerve therapy such as therapy to relieve occipital neuralgia, trigeminal neuralgia, facial pain, migraine headaches, other target nerves of patient 14, and the like.

Leadless IMD 16 includes a housing and a stimulation energy delivery element positioned on the housing or within the housing and controlled by a stimulation module to deliver stimulation to a target tissue site. In addition, leadless IMD 16 may include a pump reservoir within the housing that stores genetic material and a pump within the housing that delivers the genetic material to the target tissue site. Delivery of genetic material to the target tissue site can improve properties of cells of the target tissue site to increase the efficiency of treatment of the disorder of patient 14. The genetic material delivered to the target tissue site via the pump of IMD 16 may take any suitable form. In some examples, the genetic material may be delivered via a viral vector, such as an adenoviral or adeno-associated viral vector. Additionally or alternatively, the genetic material may be delivered via a liposomal vector or as a plasmid deoxyribonucleic acid (DNA). The delivered genetic material causes transgene expression by the tissue located at the target tissue site, which may modify properties of the tissue at the target tissue site.

In the example illustrated in FIG. 1, IMD 16 is positioned proximate to the SA node of heart 12 of patient 14. When functioning normally, the SA node of heart 12 is the pacemaker for heart 12 and generates action potentials that establish a normal rhythm of heart 12. However, when the SA node of patient 12 functions abnormally, patient 12 may require therapy and/or treatment to maintain a normal sinus rhythm of heart 12. For example, IMD 16 may deliver electrical stimulation to heart 12 to pace heart 12.

Ultimately, it is desirable to cure a patient's condition for his or her lifetime. But the implanted medical devices such as IMD 16 generally rely on a finite power source, such as a non-rechargeable battery, to provide energy for delivery of therapeutic stimulation. Thus, there may be a need to implant additional devices upon exhaustion of the energy source. The timing of the depletion of the energy source is often unpredictable and will vary from patient to patient because it is highly dependent on frequency of usage. Moreover, when the energy source of the implanted medical device is depleted, it may not be desirable or possible to explant the medical device. Yet there may be a need to obtain information from the device. Accordingly, the present disclosure enables extraction of information from a memory location of the device in spite of the depleted energy source.

In addition to leadless IMD 16, system 10 includes interrogation device 20, which communicates with leadless IMD 16. The interrogation device 20 performs an interrogation function, which includes reading and/or receiving information from the IMD 16. Optionally, interrogation device 20 may also perform a programming function to provide information to the implantable medical device 16 for storage in and/or controlling operation of device 16. The retrieval of information from the implantable medical device 16 may be through wireless communications between the interrogation device 20 and the implantable medical device 16. Interrogation device 20 may retrieve the information by sending a command to the implantable medical device 16 using any of a variety of communication techniques, such as inductive coupling or radio frequency (RF) communications. In accordance with aspects of the disclosure, the commands may be issued through a communication technique that will generate energy that is sufficient to provide power to the implantable medical device 16 to sustain the communication functions of the IMD 16 to the interrogation device 20. Remote powering of the IMD 16 precludes the need for an internal power supply residing within the IMD 16 for providing electrical power thereto and facilitates communication subsequent to depletion of the internal power supply. In response to the command from the interrogating device 20, the IMD 16 transmits the information stored in the non-volatile memory. The remote powering functionality permits the components that facilitate the transfer of information from the IMD 16 to be entirely passive and accessible in spite of depletion of the internal energy source of the IMD 16.

In some examples, interrogation device 20 may comprise a handheld computing device, computer workstation, or networked computing device. Interrogation device 20 includes a user interface that presents information to and receives input from a user. It should be noted that the user may also interact with interrogation device 20 remotely via a networked computing device. The interrogation device 20 may have external programming capabilities that allow options for manually conducting stimulation threshold tests and reprogramming the stimulation parameters in order to minimize the necessary stimulation energy. In addition, the user may interact with interrogation device 20 to retrieve physiological or diagnostic information from leadless IMD 16. A user may also interact with interrogation device 20 to program leadless IMD 16, e.g., select values for operational parameters of leadless IMD 16.

In accordance with aspects of this disclosure, the user, such as a physician, technician, surgeon, electrophysiologist, other clinician, or patient, interacts with interrogation device 20 to communicate with the leadless IMD 16 in spite of the energy source of the IMD being depleted. Furthermore, interrogation device 20 also facilitates retrieval of information from leadless IMD 16 upon exhaustion of the energy source of IMD 16 as will be described in more detail below. For example, the user may use interrogation device 20 for retrieval of information from leadless IMD 16 subsequent to depletion of the energy source of leadless IMD 16 such information including the status of IMD 16 (prior to depletion of the energy source) or the patient's physiological condition (prior to depletion of the energy source). Such information may have been stored in leadless IMD 16 prior to depletion of the energy source as is described in more detail below. In some examples, the user may use interrogation device 20 to retrieve information from leadless IMD 16 regarding sensed physiological parameters of patient 14 or information derived from sensed physiological parameters, such as intracardiac or intravascular pressure, activity, posture, respiration, tissue perfusion, heart sounds, or a cardiac electrogram (EGM), e.g., to assess the status of the genetically modified tissue prior to depletion of the energy source.

IMD 16 and interrogation device 20 may communicate via wireless communication using any techniques known in the art. Examples of communication techniques may include, for example, inductive coupling, or low frequency, or radiofrequency (RF) telemetry, or a combination thereof, with other techniques also being contemplated. The inductive coupling will also function as described below as an external energy source for a portion of IMD 16.

Figure 2:
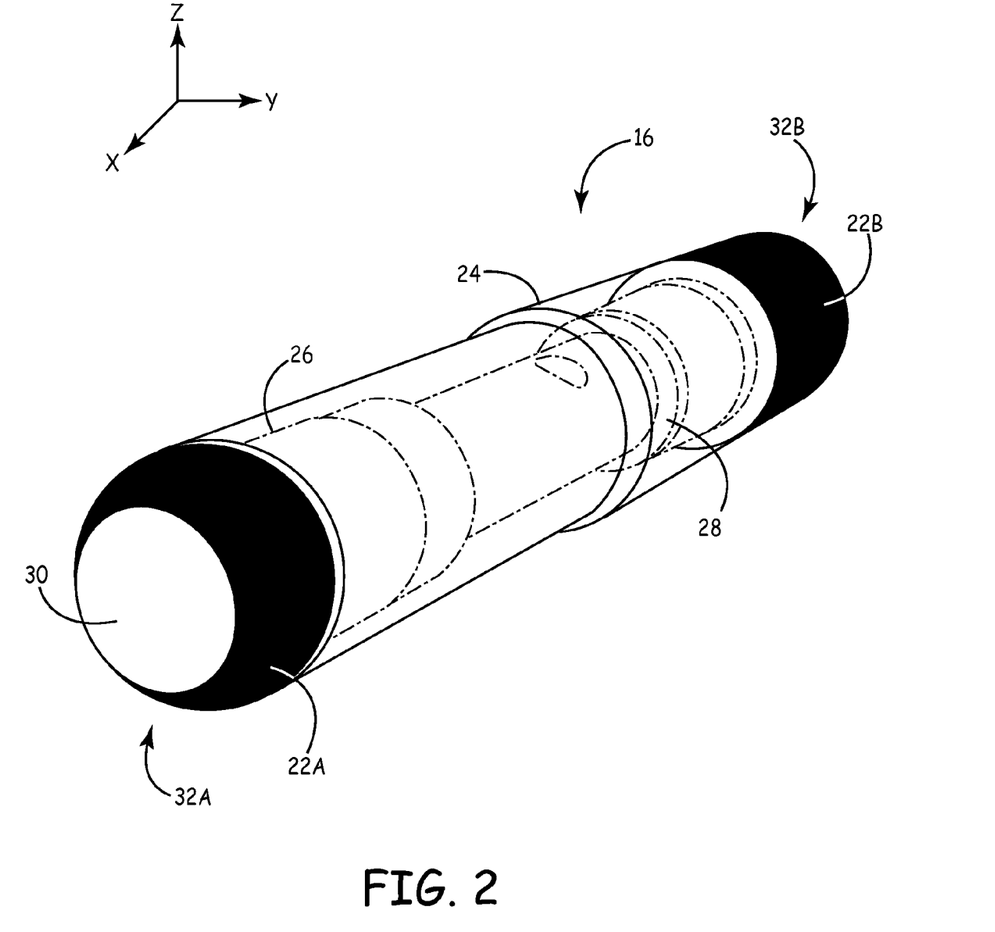
FIG. 2 is a schematic perspective view of an embodiment of an implantable medical device.

FIG. 2 is a schematic perspective view of leadless IMD 16. As illustrated in FIG. 2, IMD 16 includes two housing electrodes 22A and 22B (collectively referred to as "housing electrodes 22") positioned on housing 24 of IMD 16 and stimulation module 28. Stimulation module 28 is configured to deliver electrical stimulation to the target tissue site via housing electrodes 22. As illustrated in FIG. 2, leadless IMD 16 is formed in the shape of a cylinder extending in an x-axis direction (orthogonal x-y-z axes are shown for ease of description only) between ends 32A and 32B (collectively referred to as "ends 32"). In the example illustrated in FIG. 2, ends 32 are rounded. In some examples, rounded ends 32 may increase biocompatibility of IMD 16 with surrounding tissue upon implantation by eliminating sharp edges that may disrupt cardiac tissue at the target tissue site within heart 12. In other examples, leadless IMD 16 may be formed in another suitable shape, e.g., a circular, rectangular, or elliptical shape. While not shown in the figure, alternative embodiments of leadless IMD may additionally include a fixation element coupled to the housing of the IMD to secure the IMD proximate to the target tissue site within patient 12. The fixation elements can take the form of tines or utilize other fixation techniques known in the art, such as a helical coils, barbs, or combinations of these fixation elements.

In some examples, leadless IMD 16 may have relatively small dimensions. For example, the IMD 16 may have a length between approximately one and approximately three centimeters and a diameter between approximately one and approximately four millimeters. In some examples, implantation of IMD 16 may require a less invasive procedure if IMD 16 has relatively small dimensions, in comparison to implantation of an IMD that has larger dimensions and/or additional components, e.g., a larger pectoral or abdominal IMD coupled to a medical lead or catheter. As illustrated in FIG. 2, IMD 16 includes housing 24, within which is housed stimulation module 28. Housing 24 defines an outer surface, and IMD 16 includes two housing electrodes 22A and 22B, mechanically coupled to the outer surface of housing 24 and electrically coupled to stimulation module 28 within housing 24. Housing 24 may have any suitable configuration. In some examples, housing 24 or a portion of housing 24 may be hermetically-sealed to prevent fluid from coming into contact with stimulation module 28 and other components housed within housing 24.

Housing electrodes 22 may be any type of electrode suitable for delivering electrical stimulation to tissue of patient 14. In some examples, housing electrodes 22 may also be capable of sensing one or more signals related to physiological parameters of the target tissue site. Electrodes 22 may be formed integrally with the outer surface of housing 24 or otherwise coupled to housing 24. In this manner, electrodes 22 may be referred to as housing electrodes. In some examples, housing electrodes 22 are defined by uninsulated portions of an outward facing portion of housing 24 of IMD 16. Other division between insulated and uninsulated portions of housing 24 may be employed to define a different number or configuration of housing electrodes. For example, in an alternative configuration, IMD 16 may include a single housing electrode that comprises substantially all of housing 24, and may be used in combination with an electrode formed by a fixation mechanism of IMD 16 for delivery of therapy.

An osmotic pump 26 may be configured to deliver genetic material to the target tissue site within patient 12. The housing electrode 22A may define a space through which outlet 30 of osmotic pump 26 extends to deliver genetic material to the target tissue site. In some examples, housing 24 or a portion of housing 24 may be hermetically-sealed to prevent fluid from coming into contact with stimulation module 28 and other components housed within housing 24. In some examples, a portion of housing 24 surrounding osmotic pump 26 may be formed from a semi-permeable material that allows fluid from surrounding tissue to enter osmotic pump 26 to induce delivery of the genetic material stored in osmotic pump 26 to the target tissue.

Figure 3:
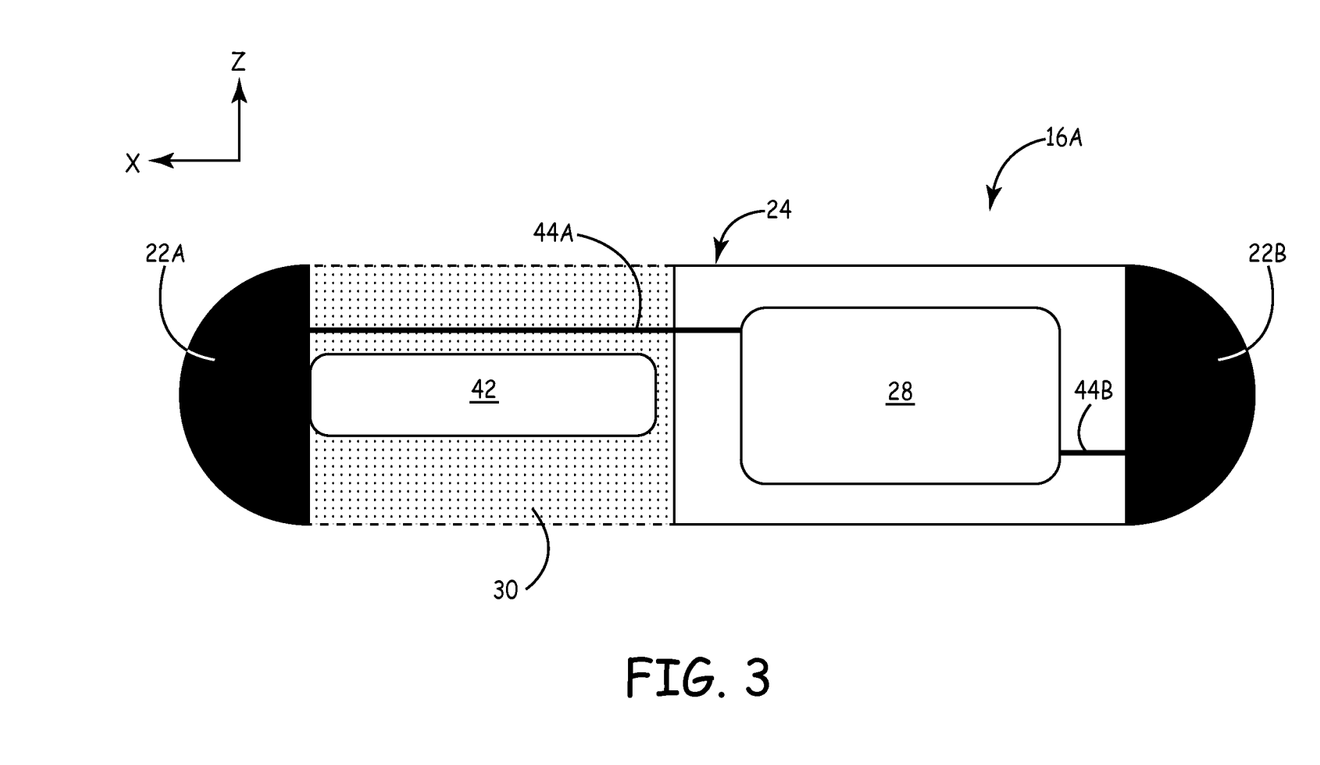
FIG. 3 is a schematic cross-sectional diagram illustrating an alternative embodiment of an implantable medical device.

FIG. 3 is a schematic cross-sectional diagram illustrating an alternative embodiment of leadless IMD 16A. The cross-section is taken in the x-z plane. (Orthogonal x-z axes are shown for ease of description only, and correspond to orthogonal x-y-z axes shown in FIG. 2.). As illustrated in FIG. 3, IMD 16 also includes stimulation module 28 and status module 30 positioned within housing 24. Stimulation module 28 may include any components necessary for delivering electrical stimulation to the target tissue site via housing electrodes 22. For example, stimulation module 28 may include a processor configured to control the delivery of electrical stimulation via housing electrodes 22 and a power source to provide operating power to IMD 16. In some examples, housing electrodes 22 also act as sensing electrodes such that housing electrodes 22 can sense signals associated with physiological parameters of tissue at the target tissue site, and stimulation module 28 may control sensing via the housing electrodes 22. Status module 30 includes components to facilitate retrieval of information from IMD 16 upon depletion of the internal power source.

As illustrated in FIG. 3, circuitry or other electronic components of stimulation module 28 may be electrically coupled to housing electrodes 22A and 22B via conductors 44A and 44B (collectively "conductors 44"), respectively. Conductors 44 may be formed from any suitable material and in any suitable configuration for effectively forming electrical connections between stimulation module 28A and housing electrodes 22 such that circuitry within stimulation module 28A can transmit and receive electrical signals to and from housing electrodes 22. For example, conductors 44 may be metal cables or bundles of metal cables.

In the example illustrated in FIG. 3, conductor 44A is coupled to housing electrode 22A. In some examples, a portion of conductor 44A may include an insulated material surrounding a conducting material to insulate the conducting material. In other examples, conductor 44A may extend through a portion of IMD 16A enclosed by a hermetically-sealed section of housing 24.

Figure 4:
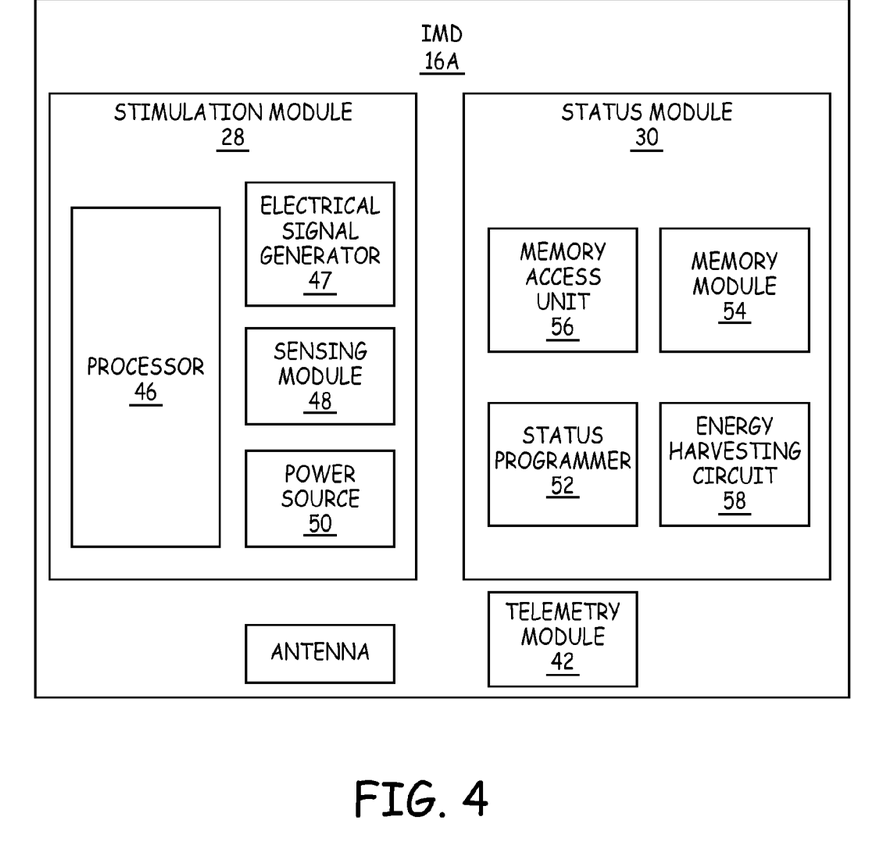
FIG. 4 illustrates a functional block diagram of an embodiment of a medical system including components of an implantable medical device that is in communication with the interrogation device.

FIG. 4 illustrates a functional block diagram of a medical system including components of an implantable medical device that is in communication with the interrogation device 20. To the extent that certain components of the circuitry of the implantable medical device are conventional in their design and operation, such components will not be described herein in detail. It is believed that design and implementation of such components would be a matter of routine practice to those of ordinary skill in the art and such components are not described in greater detail herein so as to avoid unnecessarily obscuring the details of the present disclosure. In the illustration, one embodiment of the components of IMD 16 is shown including stimulation module 28, status module 30, and stimulation energy delivery element 21 that includes housing electrodes 22.

As illustrated in FIG. 4, stimulation module 28 may include processor 46, signal generator 47, sensing module 48, and power source 50. Stimulation module 28 is configured to deliver electrical stimulation to the target tissue site within patient 14 via housing electrodes 22. For example, housing electrodes 22 and stimulation module 28 may form a cardiac stimulator to provide pacing pulses in order to treat a cardiac arrhythmia of patient 12 (e.g., bradycardia, tachycardia, or flutter of patient 12). Housing electrodes 22 may also functions as sense electrodes that can sense one or more electrical signals indicative of physiological activity at the target tissue site.

Signal generator 47 is electrically coupled to stimulation energy delivery element 21, which includes housing electrodes 22, e.g., via conductors 44 (FIG. 3). Signal generator 47 is configured to generate and deliver electrical stimulation therapy to heart 12. In examples in which IMD 16 includes more than two housing electrodes 22, signal generator 47 may include a switch module and processor 46 may use the switch module to select, e.g., via a data/address bus, which of the available electrodes 22 are used to deliver stimulation output. The switch module may include a switch array, switch matrix, multiplexer, or any other type of switching device suitable to selectively couple the therapy signal to selected electrodes.

Sensing module 48 monitors signals from at least two or more electrodes 22 in order to monitor electrical activity of heart 12. Sensing module 48 may also include a switch module to select which of the available electrodes 22 are used to sense the heart activity. In some examples, processor 46 may select the electrodes that function as sense electrodes, or the sensing electrode configuration, via the switch module within sensing module 48, e.g., by providing signals via a data/address bus.

Processor 46 of stimulation module 28 is configured to respond to sensing of physiological activity and to control delivery of electrical stimulation via housing electrodes 22. Processor 46 may include any one or more of a microprocessor, a controller, a digital signal processor (DSP), an application specific integrated circuit (ASIC), a field-programmable gate array (FPGA), or equivalent discrete or integrated logic circuitry. In some examples, processor 46 may include multiple components, such as any combination of one or more microprocessors, one or more controllers, one or more DSPs, one or more ASICs, or one or more FPGAs, as well as other discrete or integrated logic circuitry. The functions attributed to processor 46 in this disclosure may be embodied as software, firmware, hardware, or any combination thereof.

Status module 30 may include a memory module 54 that is coupled to the processor 46. The memory module 54 may include a memory location for storage of information. The term memory identifies data storage that comes in various forms such as integrated circuit chips. While there are several different types of memory, it is contemplated that the memory location herein is a non-volatile memory that retains the information even in the absence of an energy source. Processor 46 and status module 30 will function cooperatively to periodically update a memory segment of the memory module 54. For example, a status programmer 52 may perform read/write functions to write information into the memory location and read the information for subsequent transmissions. In some embodiments, the functions of status programmer 52 may be embodied within processor 46 rather than being a distinct component. The information stored by memory module 54 may include data that is stored in another internal memory of the implantable medical device or data that is provided by the implantable medical device in the first instance. That is to say, the information is only directly stored in the memory module 54.

Although the examples described herein refer to one or more processors, e.g., processor 46, a processor may be one example of a control module. Thus, in the examples described herein, the term "control module" may include anything referred to herein as a "processor." In some examples, a control module may be configured to perform one or more random logic functions, in addition to other techniques, e.g., instruction-based techniques, described herein.

Processor 46 may include a timing and control module, which may be embodied as hardware, firmware, software, or any combination thereof. The timing and control module may comprise a dedicated hardware circuit, such as an ASIC, separate from other components of processor 46, or a software module executed by a component of processor 46. In one implementation, IMD 16 is configured to update the information stored in memory module 54 via status programmer 52 in time intervals that are controlled by the timing and control module. The intervals provided by the timing and control module of processor 46 may be varied in accordance with static or dynamically configurable criteria. These criteria may include an indication of the battery level provided by, for example, a battery end-of-life indicator. For example, the initial battery level at a predetermined lifetime of the device such as at the implantation of the device may be established and the frequency of updates or time of data storage based upon the battery level reaching a predetermined level or percentage of the initial implant level. In one instance based on reaching a predetermined percentage, the data storage in memory module 54 may be performed when the battery reaches a value between 20% and 1%, or 10% and 1%, or 5% and 1% of the initial battery level. Moreover, the frequency may be increased as the battery level decreases within different ranges, such as once a month data storage when the battery level value is between 20% and 10%, once a week when the battery level value is less than 10% and 5%, and once a day when the battery level value is less than 5%. As another example, the frequency of updates may be increased upon a determination that the battery is nearing its end of life. As another example, the durations of these intervals may be determined by processor 46 in response to data stored in a memory of IMD 16. In another implementation, the information may be stored in memory module 54 in response to one or more event triggers. Such events may include sensing of R-waves or P-waves with detection channels of sensing module 48. In yet another implementation, the IMD 16 may be configured to store information pertaining to a failure mode of the device. Although IMD 16 is illustrated as a single integral device for ease of discussion, it should be noted that in embodiments where the device includes multiple component parts or peripheral components attached to the device, the information pertaining to a failure mode stored in memory module 54 may include data regarding those peripheral components or multiple constituent parts.

In an alternative embodiment, the information is transferred into memory module 54 in response to a request by the interrogation device 20. This request may occur subsequent to depletion of the energy source 50. As is known in the art, the IMD 16 will typically include one or more memory locations. In the embodiment, a memory to memory transfer will be performed from the internal IMD 16 memory location to the memory module 54 in response to the request by the interrogation device 20. Because the transfer takes place subsequent to depletion of energy source 50, it is contemplated that one or more components of the IMD 16 will be powered via energy sourced from an external location to enable the information transfer functionality as will be described below.

In the embodiment of FIG. 4, the interrogation device 20 is the same as, or a part of, the IMD programmer used during implant procedures. To facilitate communication with the externally located interrogation device 20 and other external devices, a telemetry module 42 may be provided having an antenna connected to input/output circuit as is known in the art for purposes of telemetry through an RF telemetry circuit. It is contemplated that the telemetry module 42 may also be coupled directly to the processor 46.

Status module 30 further includes a memory access unit 56 that may be coupled to memory module 54. The memory access unit 56 retrieves information stored in the memory module 54 in response to commands issued by the interrogation device 20 and transmits the information to the interrogation device 20. As previously described, embodiments of the disclosure contemplate retrieval of information from the memory module 54 subsequent to depletion of the power source 50 supplying power to the IMD 16 components. Alternatively, the memory location may be segmented and formed to have both a volatile memory portion and a non-volatile memory portion. An example of a memory module incorporating the non-volatile memory location may be a chip such as an RFID of standard construction that can be obtained from Alien Inc. or Matrix, Inc. which are several of many chip manufacturers in the RFID chip industry.

The various components of IMD 16 are coupled to power source 50, which may include a non-rechargeable battery. A non-rechargeable battery may be capable of holding a charge for several years and that duration defines the lifetime of the battery.

In general, it is contemplated that the status module 30 does not have its own internal source of energy. During the lifetime of the power source 50, the status module 30 may draw energy from the power source 50. However, subsequent to depletion of the power source 50, the status module 30 will need to be powered in particular instances for continued functionality in accordance with aspects of this disclosure. As such, the telemetry functionality is utilized to source energy for powering status module 30 and/or one or more components of the IMD 16 upon depletion of the power source 50. The antenna of the telemetry module 42 is operatively connected to the status module 30, with the antenna cooperating with the status module 30 to permit the status module 30, and other components coupled to it, to be externally powered without physical connection of a power supply thereto.

The telemetry module 42 provides the desired radio frequency interface with an associated interrogation device 20 which can be configured to provide remote RF energy. Memory access unit 56 includes an energy harvesting circuit 58 for sourcing power from an external energy source such as the interrogation device 20 to independently power the retrieval of information from the memory location. The energy harvesting circuit 58 transforms the inductive energy received during telemetry into a power source for the transfer of information from the memory location to the interrogation device 20 following depletion of the power source 50. The details of an exemplary energy harvesting circuit that is remotely charged through an RF electromagnetic field may resemble that described in U.S. Pat. No. 6,127,799, issued to Krishnan, which is incorporated herein by reference in its entirety. The sourced energy may be transferred to a storage cell, such as a capacitor, and used for the information transfer.

In particular, interrogation device 20 transmits an electromagnetic field pulse that is intercepted by the telemetry module 42. The electromagnetic field that comes from the interrogation device 20 resonates with the antenna to provide energy for the memory access unit 56 to retrieve information from the memory location which is transmitted back to the interrogation device 20.

In operation, the interrogation device 20 is used to interrogate memory module 54 to obtain information therefrom. One exemplary form of the information transmitted back to the interrogation device 20 may be through load modulation. When implemented to transmit data through load modulation, the memory access unit 56 may include a suitable circuit. Conventional circuits for performing load modulation are known in the art and include the embodiments described in U.S. Pat. No. 6,282,407, issued to Vega et al., which is incorporated herein by reference in its entirety.

The information provided to the interrogation device 20 may include static information such as the model number of the patient's IMD, the serial number of the IMD, the manufacturer, the name of patient's physician, and contact information for the physician. In addition, if the patient authorizes, information including the patient's name, the patient's medical condition, the patient's address and telephone number, and other pertinent information may also be included. Additionally, dynamic information as measured at the termination of the device operation or expiration of the device lifetime may also be stored prior to the termination and transmitted. Such information may include diagnostics information such as the patient's physiological data or the last measured threshold or sensitivity trend. The information may also include the device status including such information as the latest power status (indicating whether it was normal, ERI, or EOL), the pacing circuit status (indicating whether it was normal or existence of a failure code), the sensing circuit status (indicating whether it was normal or existence of a failure code), electrode impedance including the last measured value and/or trend.

In one implementation, the memory module 54 and memory access unit 56 may be implemented as an integral unit in the form of a radio frequency identifier (RFID) unit. Briefly, RFID communication involves a reader and a transponder. The communications between the transponder and the reader may be through inductive coupling. The transponder comprises an electronic data-carrying device, usually a single microchip, and a large area coil that functions as an antenna. The transponder may be operated passively—thus enabling it to operate without a physically coupled energy source while drawing its energy requirements for operation from the reader during the inductively-coupled communication sessions. When implemented as an RFID, the memory module 54 and memory access unit 56 will include, for example, semiconductor circuits and antennas to form the transponder. The semiconductor circuits include transceiver circuits for communication and memory circuits such as ROM, EEPROM or static RAM for storage. The RFID unit will receive its activation power through the energy transferred in the RF communications with the reader.

The status module 30 is designed to communicate with the interrogation device over frequencies that range from hundreds of kilohertz (kHz) to hundreds of megahertz (MHz). As an example, the IMD 16 and the interrogation device 20 may communicate in the 402-405 MHz frequency band in accordance with the Medical Device Radiocommunications Service (MEDRADIO) band regulations. As another example, the devices may communicate over the 401-402 MHz or 405-406 MHz frequency bands in accordance with the MEDRADIO band regulations. In yet another example, the communication frequency may be in a field ranging from 800-1000 MHz.

Figure 5:
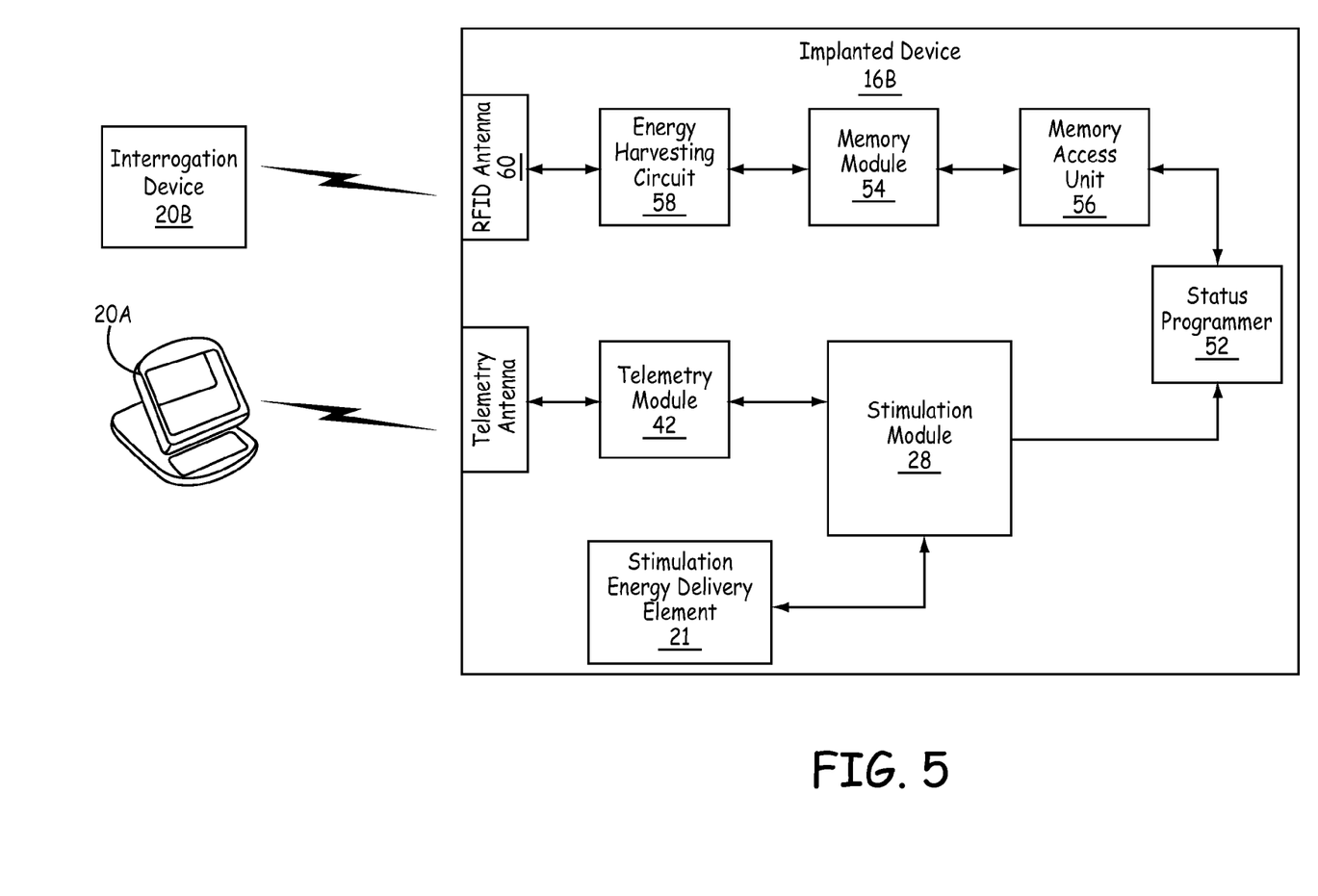
FIG. 5 illustrates a functional block diagram for an alternative embodiment of a medical system including an implantable medical device in communication with an interrogation device.

FIG. 5 illustrates a functional block diagram for an alternative medical system including an implantable medical device in communication with an interrogation device. The elements of IMD 16b corresponding to those of IMD 16 in the embodiment of FIG. 4 are numbered with identical reference designators. The reader is referred to the preceding description of FIG. 4 for a full discussion pertaining to those components. In the embodiment, a programmer 20a is provided for the conventional IMD programming functionality. The programmer 20a communicates with the IMD 16b through substantially similar or identical communication protocols as the programmers in the art. Examples of such programmers are the commercially available Medtronic Carelink® programmer, which are available from Medtronic, Inc. of Minneapolis, Minn.

The programmer 20a functions independently from an interrogation device 20b that is provided for retrieving information from the IMD 16b subsequent to depletion of the internal energy source located within IMD 16b. The IMD 16b may utilize separate communication schemes for communication with the interrogation device 20b and the programmer 20a. A first and second frequency bands may be utilized to distinguish communications with the two devices. An advantage of utilizing the separate communication schemes is that portions of the status module 30 may be deactivated for extended durations or potentially for the entire lifetime of the energy source 50 of IMD 16b. Accordingly, the memory module 54 is updated as described in conjunction with FIG. 4 with the remainder of the components of the status module 30 staying in a powered down mode until an activation signal is received when the interrogation device 20b requests information from the status module.

To facilitate the communications between IMD 16b and interrogation device 20b, a separate antenna 60 is provided. The communications between interrogation device 20b and antenna 60 may be through one of the aforementioned frequency ranges with the selected frequency range being different from the frequency range for communications with the programmer 20a.

While the present disclosure has been described in terms of certain exemplary preferred embodiments, it will be readily understood and appreciated by one of ordinary skill in the art that it is not so limited and that many additions, deletions and modifications to the preferred embodiments may be made within the scope of the disclosure as hereinafter claimed. For instance, various embodiments are described herein with respect to a leadless IMD implanted in a heart of a patient to treat a cardiac disorder of the patient. However, in other implementations, the aspects of the disclosure may be applied in other types of devices having a power source of limited duration, including IMDs having leads and other devices in the same or different environments, to access memory contents of the devices. It should also be understood that the described features, configurations or steps are presently-contemplated examples, but other examples with other features, configurations or steps or combinations thereof may also achieve one or more of the benefits of the present disclosure. Accordingly, the scope of the disclosure is limited only by the scope of the appended claims.

What is claimed is:
1. An implantable medical system, comprising:
an interrogating device for sending a communication signal including a command and energy; and
an implantable medical device, having:

an energy harvesting circuit for remotely obtaining energy from the communication signal transmitted provided by the interrogating device;

a memory module having a non-volatile memory;

a memory access unit powered by the energy harvesting circuit to access and transfer information from the non-volatile memory to the interrogating device in response to the command contained in the communication signal from the interrogating device;

an internal energy source, wherein the memory access unit is powered by the energy harvesting circuit subsequent to a depletion of energy stored by the internal energy source to access and transfer the information;

a processor configured to provide an indication of a battery level of the internal energy source and perform storage of the information in a memory location of the non-volatile memory when the internal energy source reaches a predetermined portion of an initial battery level; and an external programmer configured to retrieve the information from the implantable medical device via a first frequency band prior during a lifetime of the internal energy source, wherein the interrogating device sends the communication signal utilizing a second frequency band different than the first frequency band subsequent to depletion of the energy stored by the internal energy source, and the memory access unit remaining in a powered down mode during the lifetime of the internal energy source until the interrogation device sends the communication signal.

2. The implantable medical system of claim 1, further comprising a programmer powered by the energy harvesting circuit to write information to the memory location of the non-volatile memory.

3. The implantable medical system of claim 2, wherein the information written in the memory location is indicative of a status of the implantable medical device.

4. The implantable medical system of claim 2, further comprising a programmable non-volatile memory wherein the written information is stored within the programmable non-volatile memory during the lifetime of the internal energy source of the implantable medical device.

5. The implantable medical system of claim 1, wherein the information in the memory location is indicative of a failure mode of the implantable medical device.

6. The implantable medical system of claim 1, further comprising a passively energized processing circuitry for accessing a memory of the implantable medical device and updating the contents of the memory location.

7. The implantable medical system of claim 6, wherein the passively energized processing circuitry is powered by the energy harvesting circuit independent of an energy source of the implantable medical device.

8. The implantable medical system of claim 1, wherein the transfer of information is performed through load modulation.

9. The implantable medical system of claim 1, further comprising an event detector for providing event information associated with an operation of the implantable medical device.

10. The implantable medical system of claim 9, wherein the non-volatile memory is updated with event information.

11. The implantable medical system of claim 10, wherein the event information comprises least one of: a battery end of life indicator, status information of the medical device, and an action to be taken by the medical device.

12. The implantable medical system of claim 9, wherein the programmer writes the information to the memory location of the non-volatile memory in response to the detected event.

13. The implantable medical system of claim 2, wherein the programmer writes the information to the memory location of the non-volatile memory in response to a manual command.

14. The implantable medical system of claim 1, wherein the implantable medical device further comprises a battery monitor, wherein the non-volatile memory location is updated with information from the implantable medical device based on a given power level of the battery.

15. The implantable medical system of claim 14, wherein the battery power level is between 10% and 1% of the initial level, wherein the initial battery level is determined at a predetermined lifetime of the internal energy source of the implantable medical device.

16. The implantable medical system of claim 14, wherein the battery level is between 5% and 1% of the initial level, wherein the initial battery level is determined during implantation of the device.

17. The implantable medical system of claim 1, wherein the memory location is rewritable.

18. The implantable medical system of claim 1, wherein the memory module is an RFID.

19. The implantable medical system of claim 18, further comprising an RFID antenna.

20. The implantable medical system of claim 18, further comprising an RFID transponder.

21. The implantable medical system of claim 1, further comprising a self-test module.

22. The implantable medical system of claim 1, wherein the power provided by the interrogating device is coupled with the command.

23. An implantable medical system, comprising:
an interrogating device; and
an implantable medical device, having:
an energy harvesting circuit for remotely obtaining energy provided by the interrogating device;
a memory module having a non-volatile memory;
a memory access unit powered by the energy harvesting circuit to retrieve information from the non-volatile memory and transmit the retrieved information to the interrogating device in response to a command from the interrogating device;
an internal energy source, wherein the memory access unit is powered by the energy harvesting circuit subsequent to a depletion of energy stored by the internal energy source to retrieve and transmit the information;
a processor configured to provide an indication of a battery level of the internal energy source and perform storage of the information in a memory location of the non-volatile memory when the internal energy source reaches a predetermined portion of an initial battery level; and
an external programmer configured to retrieve information from the implantable medical device via a first frequency band prior during a lifetime of the internal energy source,
wherein the interrogating device sends the communication signal utilizing a second frequency band different than the first frequency band subsequent to depletion of the energy stored by the internal energy source, and the memory access unit remaining in a powered down mode during the lifetime of the internal energy source until the interrogation device sends the communication signal.

24. The system of claim 23, wherein the information written in the memory location is indicative of a status of the implantable medical device.

25. The system of claim 23, further comprising an event detector for providing event information associated with an operation of the implantable medical device.

26. The system of claim 23, wherein the implantable medical device further comprises a battery monitor, wherein the non-volatile memory location is updated with information from the implantable medical device based on a given power level of the battery.

* * * * *